430-553 SR
9/2/86 OR H 000,131

United States Statutory Invention Registration [19]

[11] Reg. Number: H131

Furutachi et al. [45] Published: Sep. 2, 1986

[54] SILVER HALIDE COLOR PHOTOGRAPHIC MATERIAL

[75] Inventors: Nobuo Furutachi; Tadahisa Sato; Toshio Kawagishi; Kiyoshi Nakazyo, all of Kanagawa, Japan

[73] Assignee: Fuji Photo Film Co., Ltd., Minami-ashigara, Japan

[21] Appl. No.: 773,892

[22] Filed: Sep. 9, 1985

[30] Foreign Application Priority Data

Sep. 7, 1984 [JP] Japan ..... 59-187315

[51] Int. Cl.[4] ..... G03C 7/34

[52] U.S. Cl. ..... 430/553; 430/551; 430/552; 430/558

[58] Field of Search ..... 430/551, 552, 553, 558 R

[56] References Cited

U.S. PATENT DOCUMENTS

| | | | |
|---|---|---|---|
| 3,519,429 | 7/1970 | Lestina et al. | 430/558 |
| 3,725,067 | 4/1973 | Bailey et al. | 430/558 |
| 4,443,536 | 4/1984 | Lestina | 430/558 |
| 4,500,630 | 2/1985 | Sato et al. | 430/558 |
| 4,511,649 | 4/1985 | Ogawa et al. | 430/558 |
| 4,524,132 | 6/1985 | Aoki et al. | 430/553 |
| 4,533,625 | 8/1985 | Ichijima et al. | 430/558 |
| 4,540,654 | 9/1985 | Sato et al. | 430/558 |

*Primary Examiner*—John F. Terapane
*Assistant Examiner*—Jack Thomas
*Attorney, Agent, or Firm*—Sughrue, Mion, Zinn, MacPeak and Seas

[57] ABSTRACT

Silver halide color photographic materials contain pyrazoloazole type magenta couplers having at least one hydroxyphenyl group bonded thereto. The silver halide color photographic materials are improved in color developability and color image light fastness. The pyrazoloazole type magenta couplers are 5-membered ring/5-membered ring condensed nitrogen heterocyclic type couplers.

8 Claims, No Drawings

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

SILVER HALIDE COLOR PHOTOGRAPHIC MATERIAL

FIELD OF THE INVENTION

The present invention relates to a silver halide color photographic material, particularly to a silver halide color photographic material improved in color developability and color image light fastness, and more particularly to a silver halide color photographic material containing a pyrazoloazole type magenta coupler having at least one hydroxyphenyl group.

BACKGROUND OF THE INVENTION

It is well known that, in a silver halide color photographic material, many methods employ so-called dye forming couplers that react with light-sensitive silver halide emulsions and the oxidation products of aromatic primary amine developing agents to form dyes and generally a combination of a yellow coupler, a cyan coupler and a magenta coupler is used.

Of these, 5-pyrazolone type couplers, which are frequently used as a magenta coupler, have a big problem with respect to color reproduction in that the azomethine dyes obtained from these couplers exhibit a secondary peak in the region around 430 nm (the blue region) and that the red absorption of the dyes is also undesirably high.

To solve this problem, a pyrazolobenzimidazole skeleton described in British Pat. No. 1,047,612 and a pyrazolotriazole skeleton described in U.S. Pat. No. 3,725,067 have long been suggested as magenta dye image forming couplers.

Lately, a 1H-imidazo[1,2-b]pyrazole skeleton described in Japanese Patent Application (OPI) No. 162548/84 (the term "OPI" as used herein refers to a "published unexamined Japanese patent application"), a 1H-pyrazolo[1,5-b][1,2,4]triazole skeleton described in Japanese Patent Application (OPI) No. 171956/84, a 1H-pyrazolo[1,5-a]tetrazole skeleton described in Japanese Patent Application (OPI) No. 33552/85 and a 1H-pyrazolo[1,5-b]pyrazole skeleton described in Japanese Patent Application (OPI) No. 43659/85 are suggested.

However, although the above problem with respect to hue has been solved by couplers of these types, it has been found that the maximum color density (hereinafter referred to as Dmax) decreases. This is because the conversion ratio (hereinafter referred to as color forming efficiency) from the coupler to the azomethine dye when development is carried out under conditions such that a sufficient amount of an oxidation product of the aromatic primary amine developing agent will be produced in the silver halide emulsion layer.

As a means of increasing the color forming efficiency there are known means of introducing a leaving group in the coupling active site, means of adding a color development accelerator, means of changing the ballast group to one suitable to the coupler skeleton, etc.

On the other hand, with respect to color image light fastness obtained by these skeletons, although pyrazolotriazoles described in U.S. Pat. No. 3,725,067 are very unfavorable, other skeletons are excellent in color image light fastness.

SUMMARY OF THE INVENTION

A primary object of the present invention is to provide a silver halide color photographic material improved in color developability (color forming efficiency) using a pyrazoloazole type magenta coupler improved in color developability.

Another object of the present invention is to provide a silver halide color photographic material improved in color image light fastness.

To attain the above objects, as a result of an attempt wherein various substituents have been studied on pyrazoloazole type magenta couplers high in color image light fastness, a group of couplers excellent in color developability and color image light fastness have been obtained by substituting with at least one hydroxyphenyl group.

As couplers having a hydroxyphenyl group in the molecule of a magenta coupler there are known couplers wherein a light stable group is introduced in a 5-pyrazolone skeleton as described in U.S. Pat. No. 3,519,429, and couplers wherein a hydroxyphenylsulfonyl group is introduced as described in U.S. Pat. No. 4,443,536. On the one hand, in the former, it is restricted to a 5-pyrazolone skeleton and does not include pyrazoloazole type couplers that fall within the present invention, and on the other hand, in the latter, although examples are known wherein it is applied to a 1H-pyrazolo[5,1-c][1,2,4]triazole skeleton, not only this skeleton itself, as stated beofre, is low in light fastness but also its color image light fastness could not be improved by connecting a hydroxyphenylsulfonyl group.

Therefore, the inventors have found that the objects of the present invention can be attained by providing a silver halide color photographic material characterized in that it contains a pyrazoloazole type magenta coupler represented by the following formula (I):

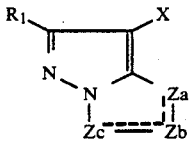

(I)

wherein $R_1$ represents a hydrogen atom or a substituent, X represents a hydrogen atom or a releasable group that can be released by the coupling reaction with an aromatic primary amine developer oxidation product, Za, Zb and Zc each represents a methine, a substituted methine, =N— or —NH—, one of the Za-Zb bond and the Zc-Zc bond is a double bond and the other is a single bond, when the Zb-Zc bond is a carbon-carbon double bond it may be part of an aromatic group, and a dimer may be formed by $R_1$ and X or a substituted methine of Za, Zb or Zc, provided that when Zc represents a methine or a substituted methine, Za and Zb do not represent at the same time =N— or —NH—; to which coupler at least one group represented by the following general formula (II) is bonded:

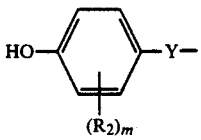

(II)

wherein $R_2$ represents a hydrogen atom, a halogen atom, an alkyl group, an aryl group, a heterocyclic group, a hydroxyl group, an acyl group, an alkoxy group, an aryloxy group, an acylamino group, a sulfonamide group, a carbamoyl group, a sulfamoyl group, a ureido group, an alkoxycarbonyl group, an alkoxycarbonylamino group, a sulfonyl group, an alkylthio group, an arylthio group, a cyano group, a nitro group, or a carboxyl group, Y represents —O—, —S—,

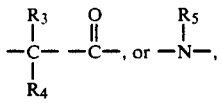

wherein $R_3$ and $R_4$ each represents a hydrogen atom, an alkyl group, a halogen atom, or an aryl group, and $R_5$ represents a hydrogen atom, an alkyl group, an aryl group, an acyl group, or a sulfonyl group, and m is an integer of from 1 to 4 and when m is 2 or more, the $R_2$'s may be the same or different.

DETAILED DESCRIPTION OF THE INVENTION

Compounds represented by general formula (I) are 5-membered ring/5-membered ring condensed nitrogen heterocyclic type couplers, and their color developing nucleus exhibits aromatic character isoelectronic to naphthalene, and have a chemical structure generally called azapentalene. Preferred compounds of couplers represented by general formula (I) are 1H-imidazo[1,2-b]-pyrazoles, 1H-pyrazolo[1,5-b]pyrazoles, 1H-pyrazolo[1,5-b][1,2,4]triazoles, 1H-pyrazolo[1,5-d]tetrazoles and 1H pyrazolo[1,5-a]benzimidazoles, which have respectively general formulae (I-1), (I-2), (I-3), (I-4) and (I-5) given below. In these compounds, (I-1) and (I-3) are particularly preferable, and (I-3) is most preferable.

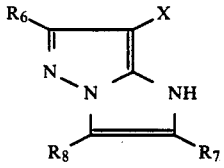

(I-1)

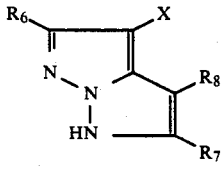

(I-2)

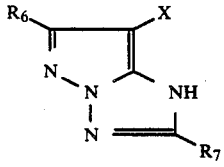

(I-3)

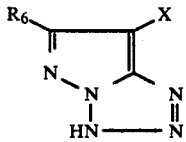

(I-4)

-continued

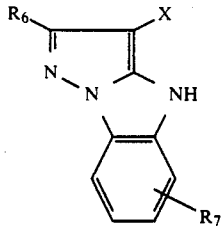

(I-5)

wherein $R_6$, $R_7$ and $R_8$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imide group, a sulfamoylamino group, a carbamoylamino group, an alkylthio group, an arylthio group, a heterocyclic thio group, an alkoxycarbonylamino group, an aryloxycarbonylamino group, a sulfonamide group, a carbamoyl group, an acyl group, a sulfamoyl group, a sulfonyl group, a sulfinyl group, an alkoxycarbonyl group, or an aryloxycarbonyl group, and X represents a hydrogen atom, a halogen atom, a carboxyl group, or a group that is bonded with the carbon atom at the coupling site through an oxygen atom, a nitrogen atom or a sulfur atom and can leave when coupling occurs.

Cases wherein $R_6$, $R_7$, $R_8$ or X is a divalent group to form a bis form are also included.

More particularly, $R_6$, $R_7$ and $R_8$ each represents a hydrogen atom, a halogen atom (e.g., a chlorine arom, a bromine atom, etc.), an alkyl group (e.g., a methyl group, a propyl group, a t-butyl group, a trifluoromethyl group, a tridecyl group, a 3-(2,4-di-t-amylphenoxy)propyl group, a 2-dodecyloxyethyl group, a 3-phenoxypropyl group, a 2-hexylsulfonylethyl group, a cyclopentyl group, a benzyl group, etc.), an aryl group (e.g., a phenyl group, a 4-t-butylphenyl group, a 2,4-di-t-amylphenyl group, a 4-tetradecanamidophenyl group, etc.), a heterocyclic group (e.g., a 2-furyl group, a 2-thienyl group, a 2-pyrimidinyl group, a 2-benzothiazolyl group, etc.), cyano group, an alkoxy group (e.g., a methoxy group, an ethoxy group, a 2-methoxyethoxy group, a 2-dodecyloxyethoxy group, a 2-methanesulfonylethoxy group, etc.), an aryloxy group (e.g., a phenoxy group, a 2-methylphenoxy group, a 4-t-butylphenoxy group, etc.), a heterocyclic oxy group (e.g., a 2-benzimidazolyloxy group, etc.), an acyloxy group (e.g., an acetoxy group, a hexadecanoyloxy group, etc.), a carbamoyloxy group (e.g., an N-phenylcarbamoyloxy group, an N-ethylcarbamoyloxy group, etc.), a silyloxy group (e.g., a trimethylsilyloxy group, etc.), a sulfonyloxy group (e.g., a dodecylsulfonyloxy group, etc.), an acylamino group (e.g., an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.), an anilino group (e.g., a phenylamino group, a 2-chloroanilino group, a 2-chloro-5-tetradecanamidoanilino group, a 2-chloro-5-dodecyloxycarbonylanilino group, an N-acetylanilino group, a 2-chloro-5-[α-(3-t-butyl-4-hydroxyphenoxy)-dodecanamido]anilino group, etc.), a ureido group (e.g., a phenylureido group, a methylureido group, an N,N-dibutylureido group, etc.), an imido group (e.g., an N-succinimido group, a 3-benzylhydantoinyl group, a 4-(2-ethylhexanoylamino)phthalimido group, etc.) , a sulfamoylamino group (e.g., an N,N-dipropylsulfamoylamino group, an N-methyl-N-decylsulfamoylamino group, etc.), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.), a heterocyclic thio group (e.g., a 2-benzothiazolylthio group, etc.), an alkoxycarbonylamino group (e.g., a methoxycarbonylamino group, is a tetradecyloxycarbonylamino group, etc.), an aryloxycarbonylamino group (e.g., a phenoxycarbonylamino group, a 2,4-di-tert-butylphenoxycarbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-tert-amylphenoxy)propyl]carbamoyl group, etc.), an acyl group (e.g., an acetyl group, a (2,4-di-tert-amylphenoxy)acetyl group, a benzoyl group, etc.), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.), a sulfonyl group (e.g., a methanesulfonyl group, an octanesulfonyl group, a benzenesulfonyl group, a toluenesulfonyl group, etc.), a sulfinyl group (e.g., an octanesulfinyl group, a dodecylsulfinyl group, a phenylsulfinyl group, etc.), an alkoxycarbonyl group (e.g., a methoxycarbonyl group, a butyloxycarbonyl group, a dodecylcarbonyl group, an octadecylcarbonyl group, etc.) or an aryloxycarbonyl group (e.g., a phenyloxycarbonyl group, a 3-pentadecyloxycarbonyl group, etc.).

When $R_6$, $R_7$, $R_8$ or X represents a divalent group to form a bis derivative, $R_6$, $R_7$ and $R_8$ each represents a substituted or unsubstituted alkylene group (e.g., a methylene group, an ethylene group, a 1,10-decylene group, $—CH_2CH_2—O—CH_2CH_2—$, etc.), a substituted or unsubstituted phenylene group (e.g., a 1,4-phenylene group, a 1,3-phenylene group,

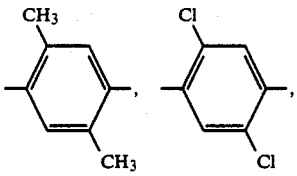

etc.), or —NHCO—$R_9$—CONH— (wherein $R_9$ represents a substituted or unsubstituted alkylene or phenylene group, e.g., $—NHCOCH_2CH_2CONH—$,

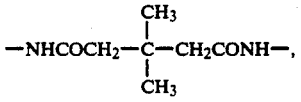

-continued

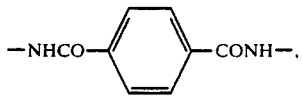

etc.) or —S—$R_{10}$—S— (wherein $R_{10}$ represents a substituted or unsubstituted alkylene group, e.g., $—S—CH_2CH_2—S—$,

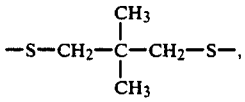

etc.), and X may represent a divalent group into which the above-described monovalent group is converted by cut of linkage at an appropriate position of the monovalent group.

In detail, X represents a hydrogen atom, a halogen atom (e.g., a chlorine atom, a bromine atom, an iodine atom, etc.), a carboxyl group, a group that bonds through an oxygen atom (e.g., an acetoxy group, a propanoyloxy group, a benzoyloxy group, a 2,4-dichlorobenzoyloxy group, an ethoxyoxazoyloxy group, a pyruvoyloxy group, a cinnamoyl group, a phenoxy group, a 4-cyanophenoxy group, a 4-methanesulfonamidophenoxy group, a 4-methanesulfonylphenoxy group, an α-naphthoxy group, a 3-pentadecylphenoxy group, a benzyloxycarbonyloxy group, an ethoxy group, a 2-cyanoethoxy group, a benzyloxy group, a 2-phenethyloxy group, a 2-phenoxyethoxy group, a 5-phenyltetrazolyloxy group, a 2-benzothiazolyloxy group, etc.), a group that bonds through a nitrogen atom (e.g., a benzenesulfonamide group, an N-ethyltoluenesulfonamide group, a heptafluorobutanamide group, a 2,3,4,5,6-pentafluorobenzamide group, an octasulfonamide group, a p-cyanophenylureido group, an N,N-diethylsulfamoylamino group, a 1-piperidyl group, a 5,5-dimethyl-2,4-dioxo-3-oxazolidinyl group, a 1-benzyl-ethoxy-3-hydantoinyl group, a 2N-1,1-dioxo-3(2H)-oxo-1,2-benzoisothiazolyl group, a 2-oxo-1,2-dihydro-1-pyridinyl group, an imidazolyl group, a pyrazolyl group, a 3,5-diethyl-1,2,4-triazole-1-yl group, a 5- or 6-bromobenzotriazole-1-yl group, a 5-methyl-1,2,3,4-triazole-1-yl group, a benzimidazolyl group, a 3-benzyl-1-hydantoinyl group, a 1-benzyl-5-hexadecyloxy-3-hydantoinyl group, a 5-methyl-1-tetrazolyl group, a 4-methoxyphenylazo group, a 4-pivaloylaminophenylazo group, a 2-hydroxy-4-propanoylphenylazo group, etc.) and a group that bonds through a sulfur atom (e.g., a phenylthio group, a 2-carboxyphenylthio group, a 2-methoxy-5-t-octylphenylthio group, a 4-methanesulfonylphenylthio group, a 4-octanesulfonamidophenylthio group, a 2-butoxyphenylthio group, a 2-(2-hexanesulfonylethyl)-5-tert-octylphenylthio group, a benzylthio group, a 2-cyanoethylthio group, a 1-ethoxycarbonyltridecylthio group, a 5-phenyl-2,3,4,5-tetrazolylthio group, a 2-benzothiazolylthio group, a 2-dodecylthio-5-thiophenylthio group, a 2-phenyl-3-dodecyl-1,2,4-triazolyl-5-thio group, etc.).

More particularly, $R_2$ represents a hydrogen atom, a halogen atom (e.g., a chlorine atom, a bromine atom, etc.), an alkyl group (e.g., a methyl group, a propyl group, a t-butyl group, a trifluoromethyl group, a tridecyl group, a 3-(2,4-di-t-amylphenoxy)propyl group, a 2-dodecyloxyethyl group, a 3-phenoxypropyl group, a 2-hexylsulfonylethyl group, a cyclopentyl group, a benzyl group, etc.), an aryl group (e.g., a phenyl group, a 4-t-butylphenyl group, a 2,4-di-t-amylphenyl group, a 4-tetradecanamidophenyl group, etc.), a heterocyclic group (e.g., a 2-furyl group, a 2-thienyl group, a 2-pyrimidinyl group, a 2-benzothiazolyl group, etc.), a cyano group, an alkoxy group (e.g., a methoxy group, an ethoxy group, a 2-methoxyethoxy group, a 2-dodecyloxyethoxy group, a 2-methanesulfonylethoxy group, etc.), an aryloxy group (e.g., a phenoxy group, a 2-methylphenoxy group, a 4-t-butylphenoxy group, etc.), an acylamino group (e.g., an acetamido group, a benzamido group, a tetradecanamido group, an α-(2,4-di-t-amylphenoxy)butyramido group, a γ-(3-t-butyl-4-hydroxyphenoxy)butyramido group, an α-[4-(4-hydroxyphenylsulfonyl)phenoxy]decanamido group, etc.), a ureido group (e.g., a phenylureido group, a methylureido group, an N,N-dibutylureido group, etc.), an alkylthio group (e.g., a methylthio group, an octylthio group, a tetradecylthio group, a 2-phenoxyethylthio group, a 3-phenoxypropylthio group, a 3-(4-t-butylphenoxy)propylthio group, etc.), an arylthio group (e.g., a phenylthio group, a 2-butoxy-5-t-octylphenylthio group, a 3-pentadecylphenylthio group, a 2-carboxyphenylthio group, a 4-tetradecanamidophenylthio group, etc.), an alkoxycarbonylamino group (e.g., a methoxycarbonylamino group, a tetradecyloxycarbonylamino group, etc.), a sulfonamido group (e.g., a methanesulfonamido group, a hexadecanesulfonamido group, a benzenesulfonamido group, a p-toluenesulfonamido group, an octadecanesulfonamido group, a 2-methyloxy-5-t-butylbenzenesulfonamido group, etc.), a carbamoyl group (e.g., an N-ethylcarbamoyl group, an N,N-dibutylcarbamoyl group, an N-(2-dodecyloxyethyl)carbamoyl group, an N-methyl-N-dodecylcarbamoyl group, an N-[3-(2,4-di-tert-amylphenoxy)propyl]carbamoyl group, etc.), an acyl group (e.g., an acetyl group, a (2,4-di-tert-amylphenoxy)acetyl group, a benzoyl group, etc.), a sulfamoyl group (e.g., an N-ethylsulfamoyl group, an N,N-dipropylsulfamoyl group, an N-(2-dodecyloxyethyl)sulfamoyl group, an N-ethyl-N-dodecylsulfamoyl group, an N,N-diethylsulfamoyl group, etc.), a sulfonyl group (e.g., a methanesulfonyl group, an octanesulfonyl group, a benzenesulfonyl group, a toluenesulfonyl group, etc.), an alkoxycarbonyl group (e.g., a methoxycarbonyl group, a butyloxycarbonyl group, a dodecylcarbonyl group, an octadecylcarbonyl group, etc.), a nitro group or a carboxyl group.

Y represents —O—, —S—,

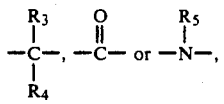

$R_3$ and $R_4$ each represents a hydrogen atom, an alkyl group (e.g., a methyl group, a t-butyl group, etc.), a halogen atom (e.g., a chlorine atom, etc.) or an aryl group (e.g., a phenyl group, a 2,4-di-t-amylphenyl group, etc.), and $R_5$ represents a hydrogen atom, an alkyl group (e.g., a methyl group, a t-butyl group, etc.), an aryl group (e.g., a phenyl group, a 2,4-di-t-amylphenyl group, etc.), an acyl group (e.g., an acetyl group, etc.) or a sulfonyl group (e.g., a methanesulfonyl group, etc.).

A group of couplers according to the present invention are completed by bonding groups defined for general formula (II) to $R_6$, $R_7$, $R_8$ or X.

With respect to the synthesis of the group of couplers according to the present invention, the skeletons can be synthesized as described in British Pat. No. 1,047,612, Japanese Patent Application (OPI) Nos. 162548/84, 171956/84 and 33552/85, etc., the substituents can be synthesized as described in U.S. Pat. Nos. 3,519,429 and 4,443,536, etc., and the bonding of the leaving groups can be carried out as described in Japanese Patent Application (OPI) No. 171956/84.

Examples of pyrazoloazole type couplers used in the present invention are given below, which would not restrict the present invention.

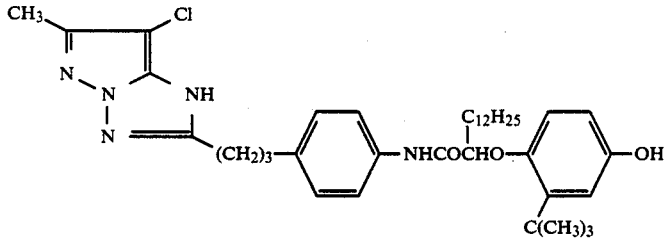

(1)

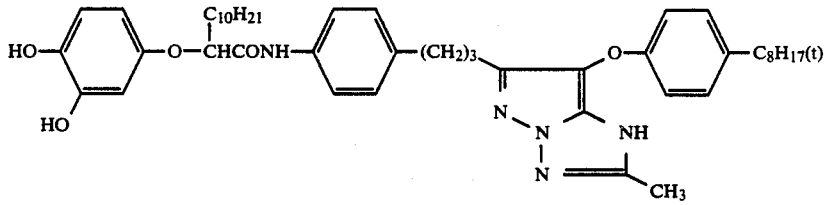

(2)

-continued
(3)
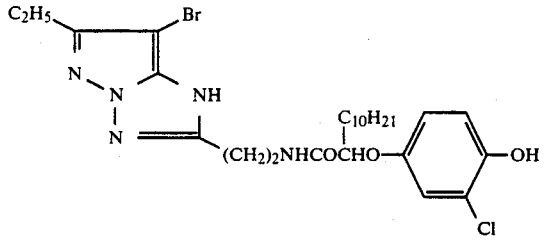
(4)
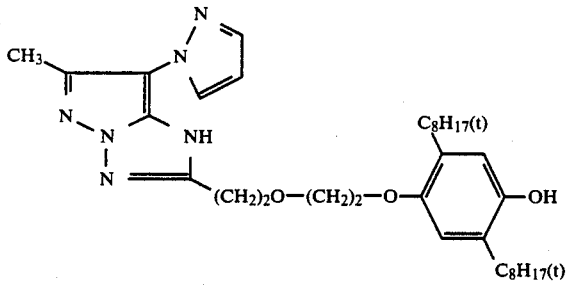
(5)
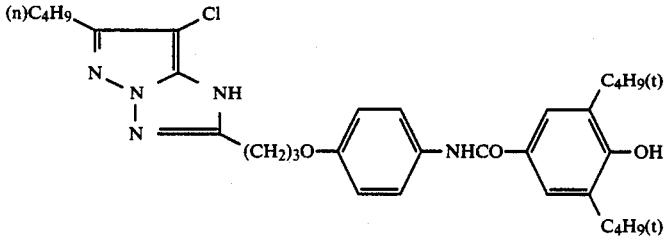
(6)
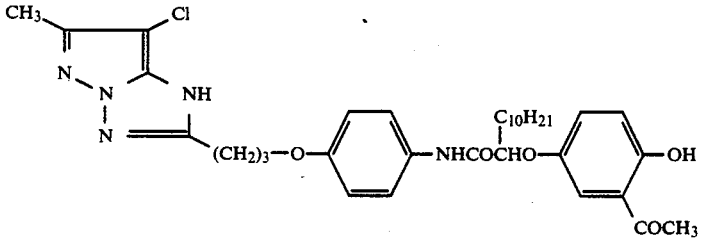
(7)
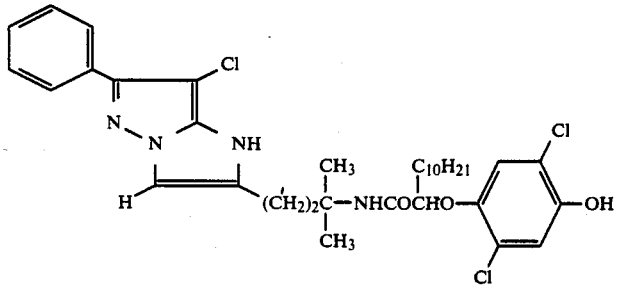
(8)
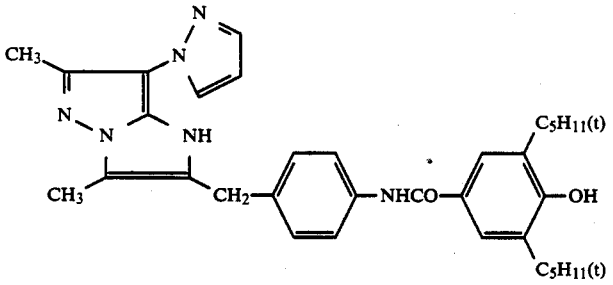

-continued
(9)
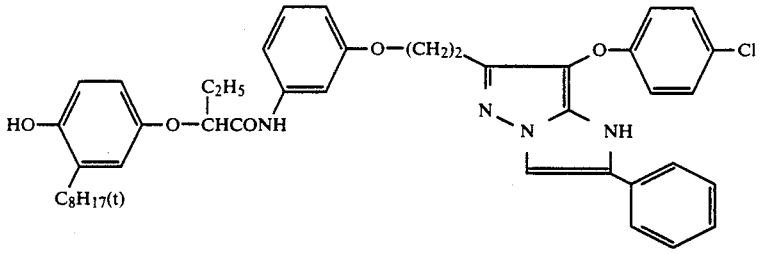
(10)
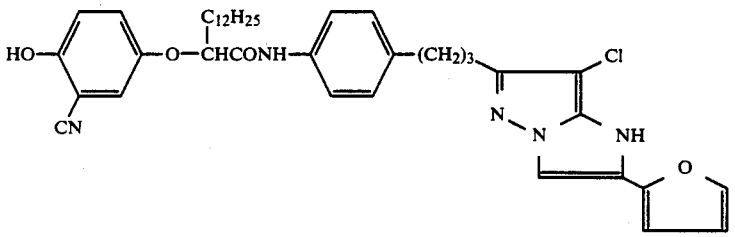
(11)
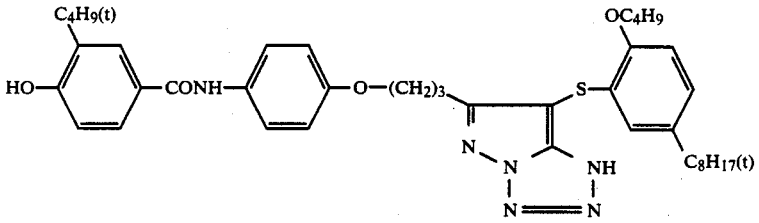
(12)
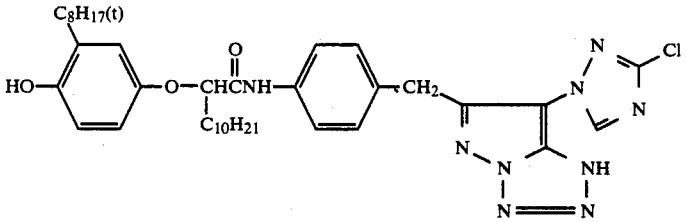
(13)
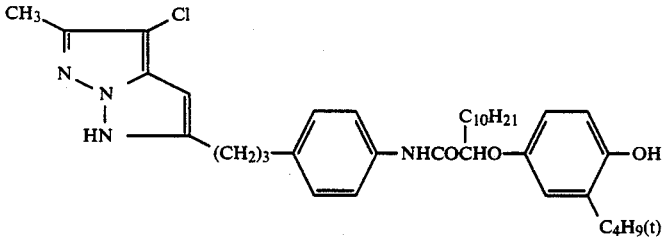
(14)
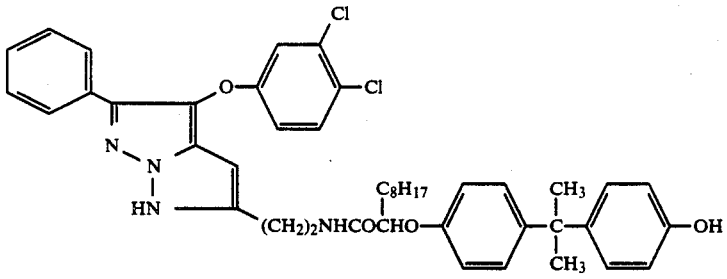
(15)
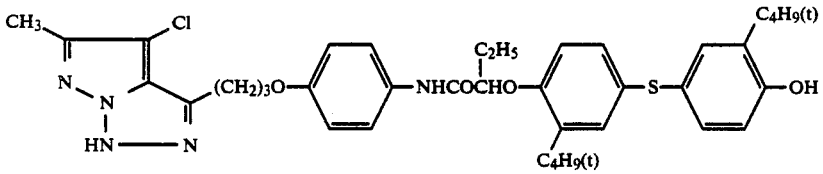

-continued
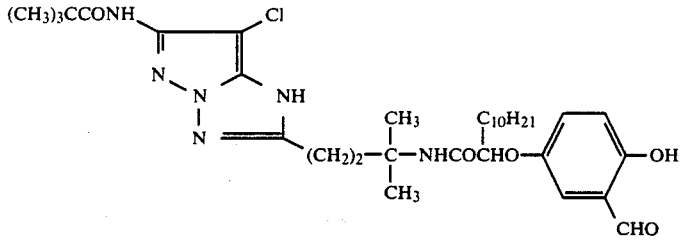
(16)
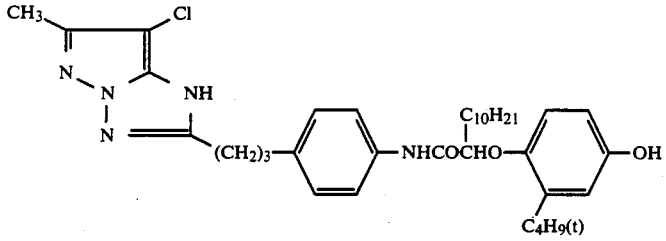
(17)
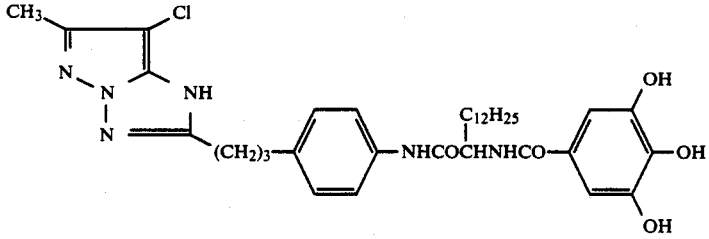
(18)
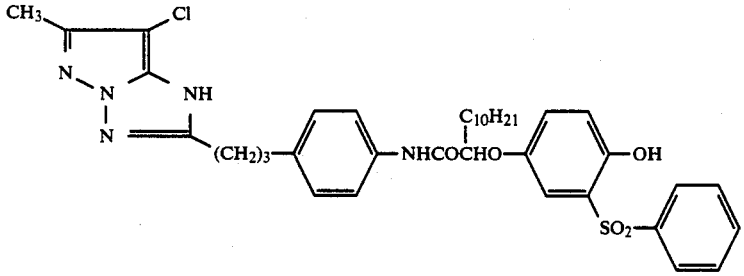
(19)
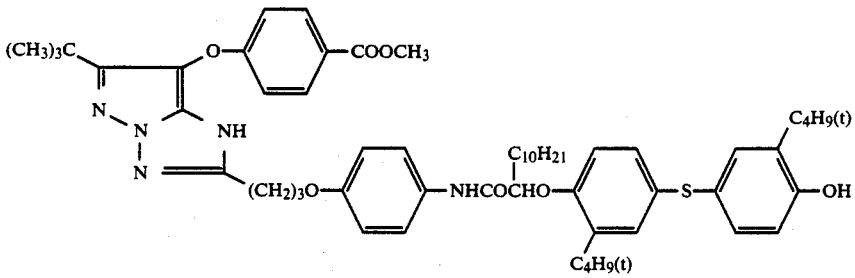
(20)
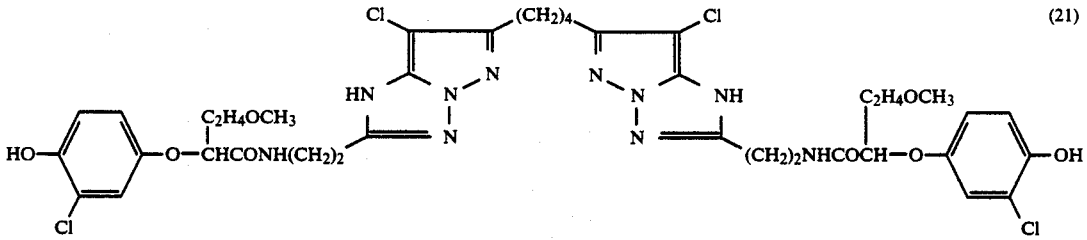
(21)
Synthesis Examples of magenta couplers according to the present invention are given below.
SYNTHESIS EXAMPLE 1
Synthesis of Exemplied Coupler (17)

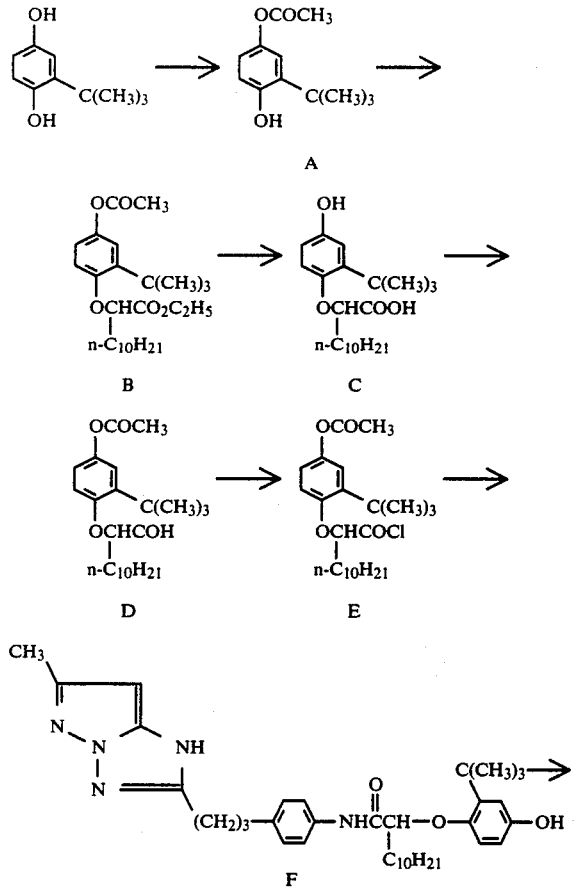

Exemplified Coupler (17)

(1) Synthesis of Intermediate D 50 g of t-butylhydroquinone and 49 ml of pyridine were added to 200 ml of acetonitrile, and the mixture was stirred while being cooled by a water bath. 32 ml of acetic anhydride was added dropwise thereto, and the mixture was stirred for 30 minutes. The reaction mixture was poured into ice water, and was extracted with ethyl acetate. The organic layer was washed with water twice, was dried over anhydrous sodium sulfate, and then condensed. The residue was recrystallized from hexane to obtain 50.7 g (81% of the theoretical yield) of Compound A.

48.5 g of Compound A, 75.2 g of ethyl 2-bromododecanate and 97 g of anhydrous potassium carbonate were added to 300 ml of N,N-dimethylformamide, and the reaction mixture was heated to 70° to 90° C. and stirred for 7 hours. After cooling, the undissolved material was filtered off, then the mixture was poured into water and extraction with ethyl acetate was carried out. The organic layer was washed with water twice and dried over anhydrous sodium sulfate to obtain 90% of a crude product of Compound B. This was dissolved in 300 ml of methanol. After an aqueous sodium hydroxide solution (33 g of sodium hydroxide in 150 ml of water) was added thereto at room temperature with stirring, the mixture was heated for 1 hour under reflux. After cooling, the reaction mixture was poured into water, then concentrated hydrochloric acid was added to make it acidic, and extraction with ethyl acetate was carried out. The organic layer was washed with water twice, and thereafter it was dried over anhydrous magnesium sulfate and was condensed. The residue was recrystallized from hexane to yield 30 g (35% of the theoretical yield) of Compound C.

20 g of Compound C and 12 ml of pyridine were added to 100 ml of acetonitrile and the mixture was stirred at room temperature. 7.7 ml of acetic anhydride was added dropwise thereto, and the mixture was stirred for 30 minutes. The reaction mixture was poured into water and was extracted with ethyl acetate. The organic layer was washed with water twice, and was dried over anhydrous sodium sulfate and then condensed. After the condensation thereof, it was subjected to silica gel column chromatography (eluting solution: chloroform), and the elute was condensed to yield 18 g (81% of the theoretical yield) of Compound D as a pale yellow oil.

Nuclear magnetic resonance spectrum ($CDCl_3$): δ (ppm) 6.98 (1H, d, J=3.0 Hz), 6.83 (1H, dd, J=3.0, 9.0 Hz), 6.63 (1H, d, J=9.0 Hz), 4.69 (1H, t, J=6.0 Hz), 2.23 (3H, s), 2.2-1.1 (27H, m), 0.89 (3H, brt)

(2) Synthesis of Exemplified Coupler (17)

18 g of Compound D and 9.1 g of phosphorus pentachloride were added to 45 ml of benzene, and after the mixture was heated for 1 hour under reflux, the solvent was distilled off under reduced pressure to yield 18.8 g (quantitative yield) of Compound E.

10.9 g of 2-[3-(4-aminophenyl)propyl]-6-methylpyrazolo[1,5-b][1,2,4]triazole and 3.8 g of sodium acetate were added to 70 ml of acetic acid, and the mixture was stirred at room temperature. A solution of Compound E in 15 ml of acetic acid that had been previously synthesized was added dropwise thereto, and the stirring was continued for 1 hour. The reaction mixture was poured into water, and was extracted with ethyl acetate, and the organic layer was washed with water twice. The organic layer was dried over anhydrous sodium sulfate, and after the condensation, it was subjected to silica gel column chromatography (eluting solution: chloroform/ethyl acetate=10:1), and the elute was condensed to dryness to yield 20 g (70% of the theoretical yield) of Compound F.

20 g of Compound F was dissolved in 200 ml of dichloromethane, then 3.3 g of N-chlorosuccinic acid imide was added thereto, and the mixture was stirred at room temperature for 10 minutes. After this reaction mixture was washed with water three times, it was dried over anhydrous sodium sulfate and then condensed. The residue was dissolved in 150 ml of methanol, and the mixture was stirred at room temperature. A solution of 3.4 g of sodium hydroxide in 20 ml of water was added dropwise thereto, and the mixture was stirred at room temperature for 10 minutes. The mixture was then poured into 500 ml of water, and neutralized with concentrated hydrochloric acid, and the separated precipitate was filtered and washed with water. The solid was purified by silica gel column chromatography (eluting solution: chloroform/ethyl acetate=9:1), and the elute was condensed to dryness to yield 13.5 g (76% of the theoretical yield) of Exemplified Coupler (17).

Elemental Analysis:

| | C | H | N |
|---|---|---|---|
| Calculated (%): | 67.95 | 7.92 | 11.01 |
| Found (%): | 67.76 | 7.95 | 10.84 |

Nuclear magnetic resonance spectrum ($CDCl_3$): δ (ppm) 12.21 (1H, br), 8.08 (2H, br), 7.2-6.7 (5H, m), 6.57

(2H, br), 4.63 (1H, br), 2.8–1.1 (33H, m), 2.29 (3H, s), 0.86 (3H, brt)

SYNTHESIS EXAMPLE 2

Synthesis of Exemplified Coupler (19)

In the following formulae, Bn represents a benzyl group.

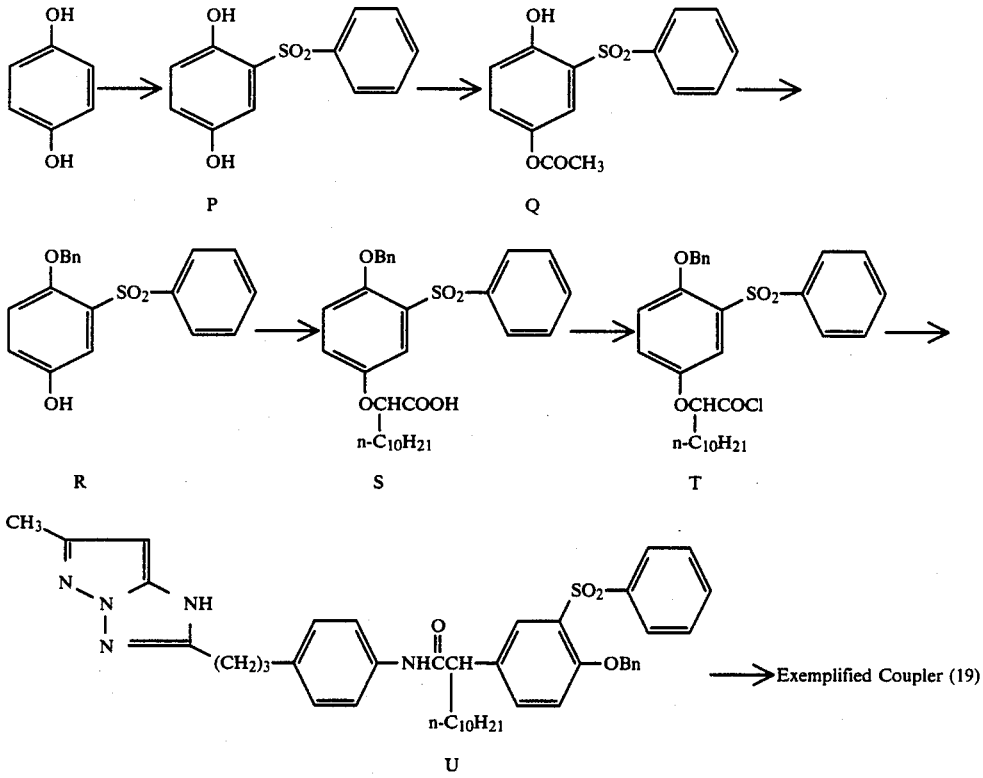

(1) Synthesis of Intermediate S 30 g of hydroquinone was added to a solvent mrxture of 300 ml of ethyl acetate and 100 ml of acetic acid, and the obtained mixture was stirred at room temperature. 57 g of sodium benzenesulfinate monohydrate was added thereto and the reaction mixture was stirred for 30 minutes. Water was added to this reaction mixture to separate the organic layer, and the organic layer was washed with water twice. The organic layer was dried over anhydrous sodium sulfate and condensed. The residue was recrystallized from acetonitrile to yield 51.1 g (78% of the theoretical yield) of Compound P.

30.9 g of boric acid was slowly added with stirring to 189 ml of acetic anhydride that had been heated to 70° C. After cooling the mixture, 25.0 g of Compound P was added thereto, and the mixture was stirred at room temperature for 6 hours. This reaction mixture was poured into 1.0 liter of water, and the separated precipitate was filtered, washed with water and dried to yield 26.4 g (87% of the theoretical yield) of a crude product of Compound Q.

26.4 g of the crude product of Compound Q and 37 g of anhydrous potassium carbonate were added to 50 ml. of N,N-dimethylformamide, and the mixture was heated to 50° C. and stirred. 15 g of benzyl bromide was added dropwise thereto, and the mixture was stirred for 3 hours at that temperature. After cooling, the undissolved material was filtered off, and the filtrate was poured into 150 ml of water and extracted with ethyl acetate. The organic layer was washed twice each time with 100 ml of saturated salt solution, and dried over anhydrous magnesium sulfate, and then condensed. The resulting condensed oil was dissolved in 150 ml of methanol. An aqueous solution of 7.2 g of sodium hydroxide in 40 ml of water was added thereto, and the mixture was stirred at room temperature for 10 minutes. This reaction mixture was poured into 600 ml of water, and after being neutralized with concentrated hydrochloric acid, it was extracted with ethyl acetate. After the organic layer was washed with water twice, it was dried over anhydrous magnesium sulfate, and then condensed. After condensation, it was subjected to silica gel column chromatography (eluting solution: chloroform/ethyl acetate = 10:1), and the elute was condensed to dryness to yield 18.1 g (59% of the theoretical yield) of Compound R.

17.3 g of Compound R and 21 g of anhydrous potassium carbonate were added to 50 ml of N,N-dimethylformamide, and the mixture was heated to 80° C. and stirred. 18.7 g of ethyl 2-bromododecanate was added dropwise thereto, and the mixture was stirred at 95° to 100° C. for 3 hours. After cooling, the undissolved material was filtered off, and the filtrate was poured into 150 ml of water, and was extracted with ethyl acetate. After the organic layer was washed twice each time with saturated salt solution, it was dried over anhydrous magnesium sulfate and was condensed. The obtained oil was dissolved in 120 ml of methanol, then a solution of 6.1 g of sodium hydroxide in 40 ml of water was added thereto, and the mixture was heated 1 hour under reflux. After cooling, the reaction mixture was poured into water, acidified with concentrated hydrochloric acid, and extracted with ethyl acetate. The organic layer was washed with water twice, and then dried over anhydrous magnesium sulfate. After it was condensed, it was subjected to silica gel column chromatography (eluting solution: chloroform/ethyl acetate=12:1), the elute was condensed to dryness to yield 20.0 g (73% of the theoretical yield) of Compound S. (2) Synthesis of Exemplified Coupler (19)

17.8 g of Compound S and 7.6 g of phosphorus pentachloride were added to 50 ml of benzene, and the mixture was heated for 1 hour under reflux. The solvent was distilled off under reduced pressure to yield Compound T. 7.7 g of 2-[3-(4-aminophenyl)propyl]-6-methylpyrazolo[1,5-b][1,2,4]triazole and 2.5 g of sodium acetate were added to 55 ml of acetic acid, and the mixture was stirred at room temperature. To this was added dropwise a solution of the previously synthesized Compound T in 15 ml of acetic acid, and the mixture was stirred for 1.5 hours. This reaction mixture was poured into water and extracted with ethyl acetate. After the organic layer was washed with water twice, the organic layer was dried over anhydrous magnesium sulfate. The organic layer was condensed and subjected to silica gel column chromatography (eluting solution: chloroform/ethyl acetate=10:1). The elute was condensed to dryness to yield 16.8 g (72% of the theoretical yield) of Compound U.

15.5 g of Compound U were dissolved in 75 ml of tetrahydrofuran, 2.0 g of 10% palladium/activated carbon were added, and the mixture was stirred at 60° C. for 16 hours at a pressure of 50 atmospheres under a hydrogen atmosphere. After the catalyst was filtered off, 150 ml of dichloromethane were added thereto, and the mixture was stirred at room temperature. 2.6 g of N-chlorosuccinic acid imide were added thereto, and the mixture was stirred for 10 minutes. This reaction mixture was washed with water three times, and dried over anhydrous magnesium sulfate and then condensed. After it had been condensed, it was subjected to silica gel column chromatography (eluting solution: chloroform/ethyl acetate=5:1). The elute was condensed to dryness to yield 12.3 g (85% of the theoretical yield) of Exemplified Coupler (19).

The pyrazoloazole type couplers used in the present invention may be used alone or in the form of mixtures.

The amount of the couplers used is in the range of $1\times10^{-3}$ to $5\times10^{-1}$ mol to preferably $1\times10^{-2}$ to $5\times10^{-1}$ per mol of silver halide.

The silver halide color photographic material according to the present invention can be used, for example, for color negative films, color positive films, color papers, color reversal films, color reversal papers, etc.

To introduce a coupler according to the present invention and a coupler used in combination therewith into a silver halide emulsion layer, a known method, for example, a method described in U.S. Pat. No. 2,322,027, can be used. For example, after the couplers are dissolved in an alkyl ester of phthalic acid (e.g., dibutyl phthalate, dioctyl phthalate, etc.), a phosphoric acid ester (e.g., diphenyl phosphate, triphenyl phosphate, tricresyl phosphate, and dioctylbutyl phosphate), a citric acid ester (e.g., tributyl acetylcitrate), a benzoic acid ester (e.g., octyl benzoate), an alkyl amide (e.g., diethyllaurylamide), fatty acid esters (e.g., dibutoxyethyl succinate, and diethyl azelate), trimesic acid esters (e.g., tributyl trimesate ), or an organic solvent having a boiling point of from 30° C. to 150° C., such as a lower alkyl acetate, for example, ethyl acetate or butyl acetate, ethyl propionate, secondary butyl alcohol, methyl isobutyl ketone, β-ethoxyethyl acetate, methyl Cellosolve acetate, or the like, they are dispersed in a hydrophilic colloid. These organic solvents having a high bciling point and organic solvents having a low boiling point may be used in admixture.

A dispersion method using polymers described in Japanese Patent Publication No. 39853/76 and U.S. Pat. Nos. 4,214,047 and 4,304,769 can also be employed.

When a coupler has an acid group such as a carboxylic acid group or sulfonic acid group, it is introduced as an aqueous alkaline solution into a hydrophilic colloid.

Gelatin is advantageously used as a binder or protective colloid in the emulsion layer or intermediate layer of the light-sensitive material according to the present invention, but other hydrophilic colloids may be used alone or together with gelatin.

In the present invention, either lime-processed gelatin or acid-processed gelatin may be used. The method of the production of gelatin is described :n detail in Arthur Vice, *The Macromolecular Chemistry of Gelatin,* Academic Press (1964).

In the photographic emulsion layer of the photographic material used in the present invention, as a silver halide may be used any of silver bromide, silver iodobromide, silver iodochlorobromide, silver chlorobromide, and silver chloride.

There is no particular restriction on the mean grain size (in the case of spherical grains or grains similar to spherical grains, the diameter of the grains is employed as the grain size and in the case of cubic grains, the long side length is employed as the grain size and is expressed by the mean value based on the projected area) of the silver halide grains in the silver halide photographic emulsion but the mean grain size is preferably not more than 3 μm.

The grain size distribution may be narrow or broad. The silver halide grains in the silver halide photographic emulsion for use in this invention may have a regular crystal form such as a cubic form, an octahedral form, etc., or an irregular crystal form such as a spherical form, a tabular form, etc., or may be a composite form of these crystal forms. Furthermore, the silver halide grains may be a mixture of these silver halide grains of various crystal forms.

Also, a silver halide emulsion wherein tabular silver halide grains having the diameter of the grains more than 5 times larger than the thickness thereof occupy not less than 50% of the total projection area may be used in this invention.

The silver halide grains for use in this invention may differ in phase between the inside thereof and the surface portion thereof. Also, the silver halide grains may be the grains mainly forming a latent image at the surface thereof or grains mainly forming a latent image in the inside thereof.

The silver halide photographic emulsions for use in this invention can be prepared using the methods described in P. Glafkides, *Chimie et Physique Photographique* (published by Paul Montel Co., 1967), G. F. Duffin, *Photographic Emulsion Chemistry* (published by The Focal Press, 1966), V. L. Zelikman et al., *Making and Coating Photographic Emulsion* (published by The Focal Press, 1964), etc.

That is, any one of acid, neutral, ammonium methods, etc., can be used, and to react a soluble silver salt and a soluble halogen salt, a single jet method, a double jet method, or a combination of these methods can be used.

The so-called reverse mixing method wherein grains are formed in the presence of excess silver ions can also be used. As one type of the double jet method can be used the so-called controlled double jet method wherein the pAg in the liquid phase in which a silver halide is to be formed is kept constant.

According to this method, a silver halide emulsion can be obtained wherein the crystal form is regular and the grain size is near uniform.

A mixture of separately prepared two or more silver halide emulsions can be used.

In the course of the formation of silver halide grains or physical ripening, a cadmium salt, zinc salt, lead salt, thallium salt, iridium salt or a complex salt thereof, a rhodium salt or a complex salt whereof, an iron salt or an iron complex salt, etc., may coexist.

The silver halide emulsion generally is chemically sensitized. To chemically sensitize a silver halide emulsion, for example, a method described in H. Frieser, *Die Grundlagen der Photographischen Prozesse mit Silberhalogeniden,* Akademische Verlagsgesellschaft, pages 675–734 (1968), can be used.

That is, sulfur sensitization method using a sulfur-containing compound reactive with active gelatin or silver (e.g., thiosulfates, thioureas, mercapto compounds and rhodanines), reduction sensitization method using a reducing substance (e.g., stannous salts, amines, hydrazine derivatives, formamidine sulfinic acid and silane compounds), or noble metal sensitization method using a noble metal compound (e.g., a gold complex salt, a complex salt of a metal in Group VIII of the Periodic Table such as platinum, iridium, palladium, etc.) or a combination of these sensitization methods can be carried out.

The photographic emulsion used in the present invention can contain various compounds for the purpose of stabilizing the photographic performance or of preventing the fogging of the light-sensitive material during the production, storage or photographic processing thereof. That is, various compounds known as an antifoggant or stabilizer can be added such as azoles, e.g., benzothiazolium salts, nitroimidazoles, nitrobenzimidazoles, chlorobenzimidazoles, bromobenzimidazoles, mercaptothiazoles, mercaptobenzothiazoles, mercaptobenzimidazoles, mercaptothiadiazoles, aminotriazoles, benzotriazoles, nitrobenzotriazoles, mercaptotetrazoles (particularly 1-phenyl-5-mercaptotetrazole), etc.; mercaptopyrimidines; mercaptotriazines; thioketo compounds such as oxazolinethione; azaindenes, e.g., triazaindenes, tetraazaindenes (particularly 4-hydroxy-substituted (1,3,3a,7)tetraazaindenes), pentaazaindenes, etc.; and benzenethiosulfonic acid, benzenesulfinic acid, benzenesulfonic acid amides, etc.

The photographic emulsion layer or other hydrophilic colloid layers of the light-sensitive material prepared by using the present invention can contain a coating aid and various surface active agents for purposes of antistatic improvement of sliding property, accelerating emulsification and dispersion, preventing of adhesion, improvement of photographic properties (e.g., development acceleration, increasing high contrast, sensitization, etc.), etc.

The photographic emulsion layer of the light-sensitive material according to the present invention can contain, for the purpose of increasing the sensitivity or contrast or accelerating the development, for example, polyalkylene oxides or their derivatives such as their ethers, esters and amines, thioether compounds, thiomorpholines, quaternary ammonium salt compounds, urethane derivatives, urea derivatives, imidazole derivatives, 3-pyrazolidones, etc.

The light-sensitive material used in the present invention may contain, in the photographic emulsion layer and other hydrophilic colloid layers, a dispersion of water-soluble or sparingly water-soluble synthesized polymers for the purpose of improving dimensional stability. For example, polymers consisting, as the monomer constituent, of alkyl (meth)acrylates, alkoxyalkyl (meth)acrylates, glycidyl (meth)acrylate, (meth)acrylamide, vinyl esters (e.g., vinyl acetate), acrylonitrile, olefins, styrene, etc., which may be used alone or in admixture or may be used in combination with acrylic acid, methacrylic acid, $\alpha,\beta$-unsaturated dicarboxylic acids, hydroxyalkyl (meth)acrylates, sulfoalkyl (meth)acrylates, styrenesulfonic acid, etc.

The photographic emulsion used in the present invention may be spectrally sensitized by methine dyes or the like. The dyes that can be used include cyanine dyes, merocyanine dyes, complex cyanine dyes, complex merocyanine dyes, holopolar cyanine dyes, hemicyanine dyes, styryl dyes and hemioxonol dyes. Particularly useful dyes are dyes belonging to cyanine dyes, merocyanine dyes, and complex merocyanine dyes. For these dyes, nuclei that can be applied are those usually utilized for cyanine dyes as basic heterocyclic nuclei. That is, the following can be applied: a pyrroline nucleus, an oxazoline nucleus, a thiazoline nucleus, a pyrrole nucleus, an oxazole nucleus, a thiazole nucleus, a selenazole nucleus, an imidazole nucleus, a tetrazole nucleus, a pyridine nucleus, etc.; a nucleus in which an alicyclic hydrocarbon ring is condensed with one of these nuclei; and a nucleus in which an aromatic hydrocarbon ring is condensed with one of these nuclei; that is, an indolenine nucleus, a benzindolenine nucleus, an indole nucleus, a benzoxazole nucleus, a naphthoxazole nucleus, a benzothiazoel nucleus, a naphthothiazole nucleus, a benzoselenazole nucleus, a benzimidazole nucleus, and a quinoline nucleus can be applied. These nuclei may be substituted on a carbon atom.

In a merocyanine dye or a complex merocyanine dye, as a nucleus having a ketomethylene structure, the following can be used: a 5- or 6-membered heterocyclic ring nucleus such as a pyrazoline-5-one nucleus, a thiohydantoin nucleus, a 2-thiooxazolidine-2,4-dione nucleus, a thiazolidine-2,4-dione nucleus, a rhodanine nucleus, a thiobarbituric acid nucleus, etc.

These sensitizing dyes may be used alone or they may be used in combination, and in particular, a combination of sensitizing dyes is often used for the purpose of supersensitization.

In addition to sensitizing dyes, the emulsion can contain a dye that has no spectral sensitizing effect itself or a substance that does not substantially absorb visible light but exhibits supersensitization effect. For example, aminostyryl compounds (for example, those described in U.S. Pat. Nos. 2,933,390 and 3,635,721), aromatic organic acid formaldehyde condensates (for example, those described in U.S. Pat. No. 3,743,510), cadmium salts, azaindene compounds, etc., may be present.

The present invention can be applied to a multilayer multicolor photographic material having at least two different spectral sensitivities on a support. A multilayer multicolor photographic material generally has at least one red-sensitive emulsion layer, at least one green-sensitive emulsion layer and at least one blue-sensitive emulsion layer on a support. The order of these layers can be optionally selected as required. Although generally the red-sensitive emulsion layer contains a cyan coupler, the green-sensitive emulsion layer contains a magenta coupler and the blue-sensitive emulsion layer contains a yellow coupler, the combination can be changed in some cases.

In photographic emulsion layers or light-insensitive layers of the photographic light-sensitive material prepared in accordance with the present invention, other dye forming couplers, i.e., compounds capable of developing colors by oxidation coupling with aromatic primary amine developing agents (e.g., phenylenediamine derivatives, aminophenol derivatives) may be used in the color development process, in addition to the coupler represented by the formula (I). The compounds and the coupler represented by the formula (I) may be used in the same or different layers.

Typical examples of these color couplers include naphthol type compounds, phenol type compounds, pyrazolone type compounds, pyrazoloazole type compounds, open chain ketomethylene compounds and heterocyclic ketomethylene compounds.

Examples of cyan, magenta and yellow couplers that can be used in the present invention are described in patents cited in *Research Disclosure,* No. 17643 (December, 1978), VII-D, and *Research Disclosure,* No. 18717 (November, 1979).

These couplers preferably have a ballast group or are polymerized to be nondiffusible. The hydrogen atom of the coupling position is preferably substituted by a leaving group. Couplers from which the dye obtained have suitable diffusibility, colored couplers, colorless couplers, and couplers releasing a development accelerator or a development restrainer along with the coupling reaction can also be used.

Examples of yellow couplers that can be used in the present invention are typically acylacetamide type couplers of the oil protect type. Examples of the acylacetamide type couplers are described in U.S. Pat. Nos. 2,407,210, 2,875,057 and 3,265,506, etc. In the present invention, 2-equivalent yellow couplers are preferably used, and typical examples thereof are oxygen atom leaving type yellow couplers described in U.S. Pat. Nos. 3,408,194, 3,447,928, 3,933,501 and 4,401,752, etc., or nitrogen atom leaving type yellow couplers described in Japanese Patent Publication No. 10739/83, U.S. Pat. Nos. 4,022,620 and 4,326,024, *Research Disclosure,* No. 18053 (April, 1979), British Pat. No. 1,425,020, West German Patent Application (OLS) Nos. 2,219,917, 2,261,361, 2,329,587 and 2,433,812. On the one hand, α-pivaloylacetanilide type couplers are distinguished in fastness to color forming dye, and on the other hand, α-benzoylacetanilide type couplers are distinguished in good color developability.

Magenta couplers that can be used in the present invention include cyanoacetyl type couplers or indazolone type couplers of the oil protect type and preferably 5-pyrazolone type couplers as well as pyrazoloazole type couplers such as pyrazolotriazoles that are outside of the present invention. Of the 5-pyrazolone type couplers, one that is substituted by an arylamino group or acylamino group in the 3-position is preferred in view of color developing speed and hue of the color forming dye, and typical examples thereof are those described in U.S. Pat. Nos. 2,311,082, 2,343,703, 2,600,788, 2,908,573, 3,062,653, 3,152,896 and 3,936,015. Leaving groups of 2-equivalent 5-pyrazolone type couplers are preferably nitrogen atom leaving groups described in U.S. Pat. No. 4,310,619 or arylthio groups described in U.S. Pat. No. 4,351,897. 5-pyrazolone type couplers having a ballast group described in European Pat. No. 73,636 are high in color developing reactivity.

Pyrazoloazole type couplers include pyrazolobenzimidazoles described in U.S. Pat. No. 3,369,897, preferably pyrazolo[5,1-c][1,2,4]triazoles described in U.S. Pat. No. 3,725,067, pyrazolotetrazoles described in *Research Disclosure,* No. 24220 (June, 1984), pyrazolopyrazoles described in *Research Disclosure,* No. 24230 (June, 1984) and imidazopyrazoles described in Japanese Patent Application (OPI) No. 171956/84.

Cyan couplers that can be used in the present invention include naphthol type couplers and phenol type couplers of the oil protect type and typical examples thereof are naphthol type couplers described in U.S. Pat. No. 2,474,293, and preferably highly active 2-equivalent naphthol type couplers of the oxygen atom leaving type described in U.S. Pat. Nos. 4,052,212, 4,146,396, 4,228,233 and 4,296,200. Examples of phenol type couplers are described in U.S. Pat. Nos. 2,369,929, 2,423,730, 2,772,162, 2,801,171 and 2,895,826.

Cyan couplers fast to heat, humidity and remperature are preferably used in the present invention, and typical examples thereof are phenol type cyan couplers described in U.S. Pat. No. 3,772,002, 2,5-diacylamino-substituted phenol type couplers described in U.S. Pat. Nos. 2,772,162, 3,758,308, 4,126,396, 4,334,011 and 4,327,173, West German Patent Application (OLS) No. 3,329,729 and Japanese Patent Application (OPI) No. 166956/84, and phenol type couplers having a phenylureido group in the 2-position and an acylamino group in the 5-position described in U.S. Pat. Nos. 3,446,622, 4,333,999, 4,451,559 and 4,427,767 and others.

To satisfy properties required in light-sensitive materials, two or more of the above couplers can be used in the same layer, or the same compound can be added in two or more layers.

To correct unrequired absorption in a short wavelength range of the color forming dye of magenta and cyan couplers, it is preferable that a color light-sensitive material for photographing uses a colored coupler additionally. Typical examples thereof are yellow colored magenta couplers described in U.S. Pat. No. 4,163,670 and Japanese Patent Publication No. 39413/82 and magenta colored cyan couplers described in U.S. Pat. Nos. 4,004,929 and 4,138,258 and British Pat. No. 1,146,368.

These color couplers that can be additionally used may form a dimer or a higher polymer. Typical examples of polymerized couplers are described in U.S. Pat. Nos. 3,451,820 and 4,080,211. Examples of polymerized magenta couplers are described in British Pat. No. 2,102,173 and U.S. Pat. No. 4,367,282.

Further, a diffusible dye forming coupler is additionally used to improve the graininess, examples of such couplers are magenta couplers described in U.S. Pat. No. 4,366,237 and British Pat. No. 2,125,570 and yellow, magenta and cyan couplers described in European Pat. No. 96,873, and West German Patent Application (OLS) No. 3,324,533.

The photographic material of the present invention can contain an inorganic or organic hardening agent in the photographic emulsion layer or other hydrophilic colloid layers. For instance, chromium salts (e.g., chromium alum, chromium acetate, etc.), aldehydes e.g., formaldehyde, glyoxal, glutaraldehyde, etc.), N-methylol compounds (e.g., dimethylolurea, methyloldimethylhydantoin, etc.), dioxane derivatives (e.g., 2,3-dihydroxydioxane), active vinyl compounds (e.g., 1,3,5-triacryloyl-hexahydro-s-triazine, 1,3-vinylsulfonyl-2-propanol, etc.), active halogen compounds (e.g., 2,4-dichloro-6-hydroxy-s-triazine, etc.), mucohalogenic acids (e.g., mucochloric acid, mucophenoxychloric acid, etc.) can be used alone or in combination.

In the light-sensitive material prepared in accordance with the present invention, if the hydrophilic colloid layer contains a dye, an ultraviolet absorbent, or the like, they may be mordanted with cationic polymers or the like.

The light-sensitive material prepared in accordance with the present invention may contain a hydroquinone derivative, an aminophenol derivative, a gallic acid derivative, an ascorbic acid derivative, etc., as a color antifoggant.

The light-sensitive material prepared in accordance with the present invention may contain an ultraviolet absorbing agent in the hydrophilic colloid layer, and, for example, the following can be used: aryl-substituted benzotriazole compounds (e.g., those described in U.S. Pat. No. 3,533,794), 4-thiazolidone compounds (e.g., those described in U.S. Pat. Nos. 3,314,794 and 3,352,681), benzophenone compounds (e.g., those described in U.S. Pat. No. 3,785,827), cinnamic acid ester compounds (e.g., those described in U.S. Pat. Nos. 3,705,805 and 3,707,375), butadiene compounds (e.g., those described in U.S. Pat. No. 4,045,229) or benzooxydol compounds (e.g., those described in U.S. Pat. No. 3,700,455). Ultraviolet absorbing couplers (e.g., α-naphthol type cyan dye forming couplers) or ultraviolet absorbing polymers can be used. These ultraviolet absorbents may be mordanted in a specific layer.

The light-senstiive material prepared in accordance with the present invention may contain, in the hydrophilic colloid layer, water-soluble dyes as a filter dye or for the purpose of preventing irradiation or other various purposes. Such dyes include oxonol dyes, hemioxonol dyes, styryl dyes, merocyanine dyes, cyanine dyes and azo dyes. Of these dyes, oxonol dyes, hemioxonol dyes and merocyanine dyes are most useful.

In practicing the present invention, the known fading preventing agents given below can be additionally used and image stabilizers that will be used in the present invention can be used alone or in combination. As known fading preventing agents can be mentioned hydroquinone derivatives, gallic acid derivatives, p-alkoxyphenols, p-oxyphenol derivatives and bisphenols.

To process photographically the layers comprising the photographic emulsion prepared by using the present invention, any of known processes and known processing liquids as described in *Research Disclosure,* Vol. 176, pages 28–30 can be applied. The processing temperature is generally in the range of from 18° C. to 50° C., but it may be lower than 18° C. or over than 50° C.

A color developer generally consists of an aqueous alkaline solution containing a color developing agent. The color developing agent may comprise a known primary aromatic amine developer such as phenylenediamines (e.g., 4-amino-N,N-diethylaniline, 3-methyl-4-amino-N,N-diethylaniline, 4-amino-N-ethyl-N-β-hydroxyethylaniline, 3-methyl-4-amino-N-ethyl-N-β-hydroxyethylaniline, 3-methyl-4-amino-N-ethyl-N-β-methanesulfoamidoethylaniline, 4-amino-3-methyl-N-ethyl-N-β-methoxyethylaniline, etc.).

Other examples of color developing agents are described in L. F. A. Mason, *Photographic Processing Chemistry,* pages 226–229, Focal Press (1966), U.S. Pat. Nos. 2,193,015, 2,592,364, 3,816,134, etc.

The developer can contain an antifoggant or a development restrainer, such as an organic antifoggant, a bromide, an iodide, and a pH buffer such as a carbonate, borate, phosphate, and sulfite of an alkali metal. If required, the developer may contain a hard warer softener, a preservative such as hydroxylamine, an organic solvent such as diethylene glycol and benzyl alcohol, a development accelerator such as amines, polyethylene glycols, and quaternary ammonium salts, a dye forming coupler, a competing coupler, a fogging agent such as sodium boron hydride, an auxiliary developing agent such as 1-phenyl-3-pyrazolidone, a tackifier, a polycarboxylic acid type chelating agent and an oxidation inhibitor.

The photographic emulsion layer after the color development is generally subjected to a bleaching process. The bleaching process may be carried out separately from or simultaneously with the fixing process. Examples of bleaching agents are compounds of polyvalent metals such as iron (III), cobalt (III), chromium (VI) and copper (II), peracids, quinones, and nitroso compounds.

For example, the following can be used: ferricyanides, dichromates, organic complex salts of iron (III) or cobalt (III) such as complex salts of organic acid such as aminopolycarboxylic acids, for example, 1,3-diamino-2-propanoltetraacetic acid, ethylenediaminetetraacetic acid and nitrilotriacetic acid, citric acid, tartaric acid and malic acid with iron (III) or cobalt (III); persulfates and permanganates; and nitrosophenol. Of these, potassium ferricyanide, sodium iron (III) ethylenediaminetetraacetate and ammonium iron (III) ethylenediaminetetraacetate are particularly useful. Iron (III) ethylenediaminetetraacetate complex salt is useful in an independent bleaching solution and also in a combined bleaching and fixing solution.

As a fixer is used one having a composition that is conventionally used. As fixing agents can be used thiosulfates, thiocyanates, and organic sulfur compounds that are known to have the effect as fixing agents. The fixer may contain as a hardening agent a water-soluble aluminum salt.

The invention will now be further explained with reference to the following Examples, which are not meant to limit the present invention.

Unless otherwise specified, all ratios, percents, etc., are by weight.

EXAMPLE 1

18 ml of tri(2-ethylhexyl)phosphate and 25 ml of ethyl acetate were added to 9.1 g of Exemplified Coupler (17) and were heated to be dissolved, and the mixture was added to 100 ml of an aqueous solution containing 10 g of gelatin and 1.0 g of sodium dodecylbenzenesulfonate, thereby a fine emulsified dispersion of the above coupler was obtained in a mechanical manner. The whole of the emulsified dispersion was added to 100 g (containing 6.5 g of Ag) of a silver chlorobromide emulsion comprising 50 mol % of Br, then 10 ml of 2% sodium salt of 2,4-dichloro-6-hydroxy-s-triazine as hardening agent were added, and the mixture was coated on a paper support both of the surfaces of which have been laminated with a polyethylene in such an amount of silver of 200 mg/m$^2$, and a gelatin layer was provided on this coated layer to obtain Sample A.

Sample B was prepared in the same manner as described above except for using 10.3 g of Exemplified Coupler (19) instead of Coupler (17) and 21 ml of tri(2-ethylhexyl)phosphate.

Further, Samples a, b and c were prepared in the same manner as described above, respectively, except for using, as comparative couplers, 8.9 g, 10.3 g and 8.9 g of Compounds (1), (2) and (3) given below instead of Coupler (17) and 18 ml, 21 ml and 18 ml of tri(2-ethylhexyl)phosphate, respectively.

Comparative Compound (1)

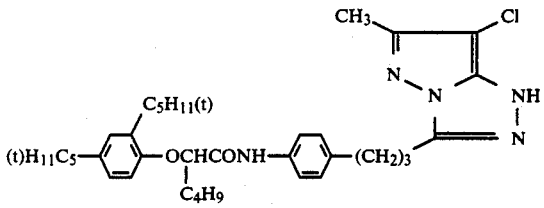

Comparative Compound (2)

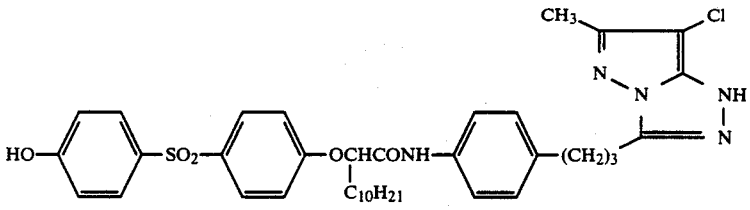

Comparative Compound (3)

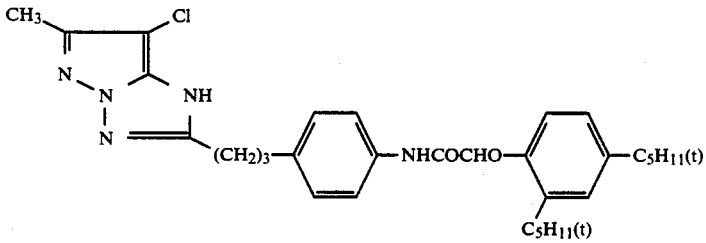

These samples were subjected to wedge exposure of 1,000 CMS and processed with the following processing solution to obtain magenta color forming images.

| | |
|---|---|
| Developer | |
| Benzyl Alcohol | 15 ml |
| Diethylenetriaminepentaacetate | 5 g |
| KBr | 0.4 g |
| $Na_2SO_3$ | 5 g |
| $Na_2CO_3$ | 30 g |
| Hydroxylamine Sulfate | 2 g |
| 4-Amino-3-methyl-N—β-(methanesulfonamido)ethylaniline.3/2$H_2SO_4$.$H_2O$ | 4.5 g |
| Water to make | 1,000 ml |
| | pH 10.1 |
| Bleach-Fixing Solution | |
| Ammonium Thiosulfate (70 wt %) | 150 ml |
| $Na_2SO_3$ | 5 g |
| Na[Fe(EDTA)] | 40 g |
| EDTA* | 4 g |
| Water to make | 1,000 ml |
| | pH 6.8 |

| Processing Steps | Temperature (°C.) | Time |
|---|---|---|
| Developer | 33 | 3 min 30 sec |
| Bleach-Fix Bath | 33 | 1 min 30 sec |
| Washing with Water | 28-35 | 3 min |

*EDTA means ethylenediaminetetraacetate acid

The thus obtained magenta color image of each of the samples was clear and high in saturation. The photographic properties of these color images were determined and the results are given as follows.

TABLE 1

| Sample | Photographic Properties: Relative Sensitivity* | Gradation | Maximum Density |
|---|---|---|---|
| a (Comparative Compound 1) | 100 | 2.77 | 2.84 |
| b (Comparative Compound 2) | 85 | 3.05 | 2.98 |
| c (Comparative Compound 3) | 93 | 2.90 | 2.93 |
| A (17) | 76 | 3.26 | 3.17 |
| B (19) | 78 | 3.21 | 3.15 |

*Fog + relative value of exposure that gives a density of 0.5. Comparative Sample a was used as reference (100).

A UV filter for cutting UV light whose wavelength is shorter than 390 nm was attached in front of the front surface of each of the other samples that had been exposed and processed according to the method stated above and each sample was exposed for 7 days using a xenon fading tester (100,000 lux) to test the fastness to light of the magenta color image. The results are given in Table 2.

TABLE 2

| Sample | Fastness to Color Image: Change in Density of Color Image |
|---|---|
| a (Comparative Compound (1)) | 0.34 (0.14) |
| b (Comparative Compound (2)) | 0.26 (0.14) |
| c (Comparative Compound (3)) | 0.57 (0.13) |
| A (17) | 0.72 (0.13) |
| B (19) | 0.71 (0.13) |

The value is magenta density of a particular section, which had had an initial density of 1.0, after the section was subjected to the fading test. The value in parentheses is the value of density (stain) obtained by measuring the section using a blue filter where color development was not observed.

With respect to the color image fastness, after on the one hand the samples were tested at 60° C. and a relative humidity of 90% for 6 weeks, and on the other hand, the samples were tested at 100° C. for 7 days, discoloration was hardly observed and occurrence of stain was not observed.

As is seen from the data, the couplers according to the present invention are excellent in photographic properties such as sensitivity, gradation, maximum density, etc. It is considered that this is due to the high coupling activity and the high efficiency of conversion to a dye. It has also become clear that the couplers according to the present invention are excellent in that they provide dyes excellent in stability and fastness to light, and produce less stain due to the remaining couplers.

EXAMPLE 2

Onto a paper support the opposite surfaces of which had been laminated with a polyethylene were coated successively a first (the lowest) layer to a seventh (the top) layer as shown in Table 3 to prepare color photographic materials.

The coating liquid compositions containing the emulsified dispersions and emulsions of the magenta couplers used in the third layer were prepared and coated in a manner simular to Example 1.

TABLE 3

| | |
|---|---|
| 7th Layer | Gelatin (coated amount: 1,600 mg/m$^2$) |
| 6th Layer | Gelatin (coated amount: 1,000 mg/m$^2$) |
| | Ultraviolet Absorbent (*1) (coated amount: 360 mg/m$^2$) |
| | Solvent (*2) (coated amount: 120 mg/m$^2$) |
| 5th Layer | Red-Sensitive Silver Chlorobromide Emulsion (Br: 50 mol %; coated silver amount: 300 mg/m$^2$) |
| | Gelatin (coated amount: 1,200 mg/m$^2$) |
| | Cyan Coupler (*3) (coated amount: 400 mg/m$^2$) |
| | Solvent (*2) (coated amount: 250 mg/m$^2$) |
| 4th Layer | Gelatin (coated amount: 1,600 mg/m$^2$) |
| | Ultraviolet Absorbent (*1) (coated amount: 700 mg/m$^2$) |
| | Color Stain Preventing Agent (*4) (coated amount: 200 mg/m$^2$) |
| | Solvent (*2) (coated amount: 300 mg/m$^2$) |
| 3rd Layer | Green-Sensitive Silver Chlorobromide Emulsion (Br: 50 mol %; coated silver amount: 180 mg/m$^2$) |
| | Magenta Coupler (*5) (coated amount: $3.4 \times 10^{-4}$ mol/m2) |
| | Solvent (*6) (coated amount: Sample C 420 mg/m$^2$, Sample D 475 mg/m$^2$, Sample d 410 mg/m$^2$, Sample 745 745 mg/m$^2$, and sample f 410 mg/m$^2$) |
| 2nd Layer | Gelatin (coated amount: 1,100 mg/m$^2$) |
| | Color Stain Preventing Agent (*4) (coated amount: 200 mg/m$^2$) |
| | Solvent (*2) (coated amount: 100 mg/m$^2$) |
| 1st Layer | Blue-Sensitive Silver Chlorobromide Emulsion (Br: 80 mol %; coated silver amount: 350 mg/m$^2$) |
| | Gelatin (coated amount: 1,500 mg/m$^2$) |
| | Yellow Coupler (*7) (coated amount: 500 mg/m$^2$) |
| | Solvent (*8) (coated amount: 400 mg/m$^2$) |
| Support | Paper support laminated with polyethylene on both sides |

(*1) UV Light Absorbent: 2-(2-Hydroxy-3-sec-butyl-5-tert-butylphenyl)benzotriazole
(*2) Solvent: Dibutyl phthalate
(*3) Cyan Coupler: 2-[α-(2,4-Di-tert-pentylphenoxy)butanamido]-4,6-dichloro-5-methylphenol
(*4) Color Stain Preventing Agent: 2,5-Dioctylhydroquinone
(*5) Magenta Coupler:
Sample D: (17)
Sample E: (19)
Sample d: Comparative Compound (1)
Sample e: Comparative Compound (2)
Sample f: Comparative Compound (3)
(*6) Solvent: Tri(2-ethylhexyl)phosphate
(*7) Yellow Coupler: α-Pivaloyl-α-(2,4-dioxo-5,5'-dimethyloxazolidin-3-yl-2-chloro-5-[α-(2,4-di-tert-pentylphenoxy)butanamido]acetanilide
(*8) Solvent: Dioctylbutyl phosphate A B-G-R separation filter was applied to each of these samples, and the samples were exposed in the same manner as Example 1, and all of them were processed in the same manner with the color developing time being varied to 2 min, 3 min 30 sec and 6 min.

The results of changes in photographic properties when the color developing time was varied are given in Table 4.

TABLE 4

| | Photographic Property | | | | | | | | |
|---|---|---|---|---|---|---|---|---|---|
| | Relative Sensitivity* Developing Time | | | Gradation Developing Time | | | Maximum Density Developing Time | | |
| Sample | 2 Min | 3 Min 30 Sec | 6 Min | 2 Min | 3 Min 30 Sec | 6 Min | 2 Min | 3 Min 30 Sec | 6 Min |
| d (Comparative Compound (1)) | 132 | 100 | 83 | 2.51 | 2.73 | 2.88 | 2.62 | 2.83 | 2.86 |
| e (Comparative Compound (2)) | 104 | 86 | 80 | 2.92 | 3.03 | 3.05 | 2.88 | 2.99 | 3.01 |
| f (Comparative Compound (3)) | 125 | 95 | 82 | 2.69 | 2.87 | 3.00 | 2.81 | 2.93 | 2.95 |
| C (Present Invention (17)) | 91 | 76 | 72 | 3.18 | 3.25 | 3.23 | 3.11 | 3.17 | 3.17 |
| D (Present Invention (19)) | 96 | 79 | 73 | 3.13 | 3.21 | 3.20 | 3.09 | 3.16 | 3.15 |

*Fog + relative value of exposure that gives a density of 0.5.
The sensitivity obtained when developing time was 3 min 30 sec using Comparative Compound (1) was used as reference (100).

On the other hand, besides the above color images, samples each having the same color image were processed and fading tests were carried out in one of which the samples were subjected to a xenon fading tester (100,000 lux) for 7 days, in one of which the samples were placed at 60° C. and a relative humidity of 90% for 6 weeks, and in one of which the samples were placed at 100° C. for 7 days. The results are given in Table 5.

TABLE 5

| | Fastness To Color Image | | |
|---|---|---|---|
| | Test Condition | | |
| Sample | Xenon (100,000 lux) for 7 Days | At 60° C. and a Relative Humidity of 90% for 6 Weeks | At 100° C. for 7 Days |
| d (Comparative Compound (1)) | 0.38 (0.16) | 97 (0.15) | 97 (0.16) |
| e (Comparative Compound (2)) | 0.29 (0.16) | 96 (0.15) | 98 (0.16) |
| f (Comparative Compound (3)) | 0.59 (0.15) | 98 (0.15) | 98 (0.15 |

TABLE 5-continued

| Sample | Fastness To Color Image Test Condition: Xenon (100,000 lux) for 7 Days | At 60° C. and a Relative Humidity of 90% for 6 Weeks | At 100° C. for 7 Days |
|---|---|---|---|
| C (Present Invention (17)) | 0.74 (0.14) | 99 (0.14) | 99 (0.14) |
| D (Present Invention (19)) | 0.74 (0.14) | 99 (0.14) | 98 (0.14) |

The value is magenta density of a particular section, which had had an initial density of 1.0, after the section was subjected to the fading test.
The value in parentheses is the value of density (stain) obtained by measuring the section with a blue filter where color development was not observed.

From the results shown in Tables 4 and 5, it is noted that since the couplers according to the present invention are high in coupling activity and color forming efficiency, the dependency of the sensitivity, gradation and maximum density on the color development time is low, the change in photographic properties within a short development time is low, the magenta color images obtained thereby are stable under light, and high temperatures and humidities, and magenta stain that will be caused by the remaining coupler is not observed completely.

While the invention has been described in detail and with reference to specific embodiments thereof, it will be apparent to one skilled in the art that various changes and modifications can be made therein without departing from the spirit and scope thereof.

What is claimed is:

1. A silver halide color photographic material characterized in that it contains a pyrazoloazole type magenta coupler represented by the following formula (I):

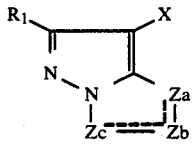

(I)

wherein $R_1$ represents a hydrogen atom or a substituent, X represents a hydrogen atom or a releasable group that can be released by the coupling reaction with an aromatic primary amine developer oxidation product, Za, Zb and Zc each represents a methine, a substituted methine, =N— or —NH—, one of the Za-Zb bond and the Zb-Zc bond is a double bond and the other is a single bond, when the Zb-Zc bond is a carbon-carbon double bond it may be part of an aromatic group, and a dimer may be formed by $R_1$ and X or a substituted methine of Za, Zb or Zc, provided that when Zc represents a methine or a substituted methine, Za and Zb do not represent at the same time =N— or —NH—; to which coupler at least one group represented by the following general formula (II) is bonded:

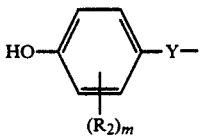

(II)

wherein $R_2$ represents a hydrogen atom, a halogen atom, an alkyl group, an aryl group, a heterocyclic group, a hydroxyl group, an acyl group, an alkoxy group, an aryloxy group, an acylamino group, a sulfonamide group, a carbamoyl group, a sulfamoyl group, a ureido group, an alkoxycarbonyl group, an alkoxycarbonylamino group, a sulfonyl group, an alkylthio group, an arylthio group, a cyano group, a nitro group, or a carboxyl group, Y represents —O—, —S—,

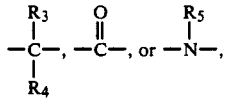

wherein $R_3$ and $R_4$ each represents a hydrogen atom, an alkyl group, a halogen atom, or an aryl group, and $R_5$ represents a hydrogen atom, an alkyl group, an aryl group, an acyl group, or a sulfonyl group, and m is an integer of from 1 to 4 and when m is 2 or more, the $R_2$'s may be the same or different.

2. A silver halide color photographic material as in claim 1, wherein the coupler represented by tne general formula (I) is 1H-imidazo[1,2-]pyrazoles, 1H-pyrazolo[1,5-b]pyrazoles, 1H-pyrazolo[1,5-b][1,2,4]-triazoles, 1H-pyrazolo[1,5-d]tetrazoles, or 1H-pyrazole[1,5-a[benzimidazoles represented by the following general formulae (I-1), (I-2), (I-3), (I-4) and (I-5):

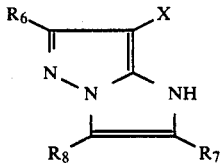

(I-1)

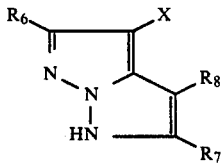

(I-2)

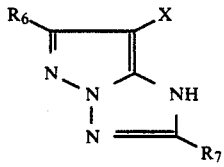

(I-3)

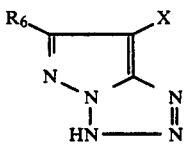

(I-4)

-continued

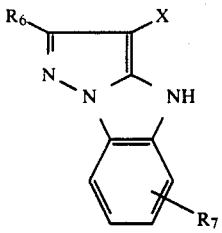

(I-5)

wherein $R_6$, $R_7$ and $R_8$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imide group, a sulfamoylamino group, a carbamoylamino group, an alkylthio group, an arylthio group, a heterocyclic thio group, an alkoxycarbonylamino group, an aryloxycarbonylamino group, a sulfonamide group, a carbamoyl group, an acyl group, a sulfamoyl group, a sulfonyl group, a sulfinyl group, an alkoxycarbonyl group, or an aryloxycarbonyl group, and X represents a hydrogen atom, a halogen atom, a carboxyl group, or a group that is bonded with the carbon atom at the coupling site through an oxygen atom, a nitrogen atom or a sulfur atom and can leave when coupling occurs, and $R_6$, $R_7$, $R_8$ or X may be a divalent group to form a bis form of the compound.

3. A silver halide color photographic material as in claim 2, wherein $R_6$, $R_7$ and $R_8$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imido group, a sulfamoylamino group, an alkylthio group, an arylthio group, a heterocyclic thio group, an alkoxycarbonylamino group, an aryloxycarbonylamino group, a sulfonamido group, a carbamoyl group, an acyl group, a sulfamoyl group, a sulfonyl group, a sulfinyl group, an alkoxycarbonyl group, or an aryloxycarbonyl group.

4. A silver halide color photographic material as in claim 2, wherein X represents a hydrogen atom, a halogen atom, a carboxyl group, a group that bonds through an oxygen atom, a group that bonds through a nitrogen atom, or a group that bonds through a sulfur atom.

5. A silver halide color photographic material as in claim 1, wherein said coupler represented by the general formula (I) has the general formula (I-1) or (I-3):

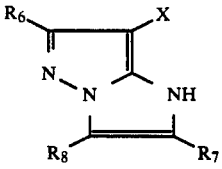

(I-1)

-continued

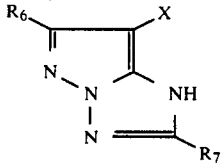

(I-3)

wherein $R_6$, $R_7$ and $R_8$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imide group, a sulfamoylamino group, a carbamoylamino group, an alkylthio group, an arylthio group, a heterocyclic thio group, an alkoxycarbonylamino group, an aryloxycarbonylamino group, a sulfonamide group, a carbamoyl group, an acyl group, a sulfamoyl group, a sulfonyl group, a sulfinyl group, an alkoxycarbonyl group, or an aryloxycarbonyl group, and X represents a hydrogen atom, a halogen atom, a carboxyl group, or a group that is bonded with the carbon atom at the coupling site through an oxygen atom, a nitrogen atom or a sulfur atom and can leave when coupling occurs, and $R_6$, $R_7$, $R_8$ or X may be a divalent group to form a bis form of the compound.

6. A silver halide color photographic material as in claim 1, wherein said coupler represented by the general formula (I) has the general formula (I-3):

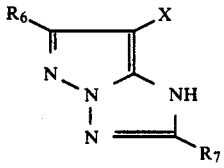

(I-3)

wherein $R_6$ and $R_7$ each represents a hydrogen atom, a halogen atom, an alkyl group, an aryl group, a heterocyclic group, a cyano group, an alkoxy group, an aryloxy group, a heterocyclic oxy group, an acyloxy group, a carbamoyloxy group, a silyloxy group, a sulfonyloxy group, an acylamino group, an anilino group, a ureido group, an imide group, a sulfamoylamino group, a carbamoylamino group, an alkylthio group, an arylthio group, a heterocyclic thio group, an alkoxycarbonylamino group, an aryloxycarbonylamino group, a sulfonamide group, a carbamoyl group, an acyl group, a sulfamoyl group, a sulfonyl group, a sulfinyl group, an alkoxycarbonyl group, or an aryloxycarbonyl group, and X represents a hydrogen atom, a halogen atom, a carboxyl group, or a group that is bonded with the carbon atom at the coupling site through an oxygen atom, a nitrogen atom or a sulfur atom and can leave when coupling occurs, and $R_6$, $R_7$, or X may be a divalent group to form a bis form of the compound.

7. A silver halide color photographic material as in claim 1, wherein the amount of the coupler is in a range of $1\times10^{-3}$ to $5\times10^{-1}$ mol per mol of silver halide.

8. A silver halide color photographic material as in claim 7, wherein the amount of the coupler is in a range of $1\times10^{-2}$ to $5\times10^{-1}$ mol per mol of silver halide.

* * * * *